United States Patent [19]

Kurihara-Bergstrom et al.

[11] Patent Number: 4,853,227

[45] Date of Patent: Aug. 1, 1989

[54] TRANSDERMAL ADMINISTRATION OF A SYSTEMIC ACTIVE AGENT TO A PREMATURE NEONATAL INFANT

[75] Inventors: Tamie Kurihara-Bergstrom, New City; William R. Good, Suffern, both of N.Y.; Charles D. Ebert, Salt Lake City, Utah

[73] Assignee: Ciba-Geigy Corporation, Ardsley, N.Y.

[21] Appl. No.: 112,917

[22] Filed: Oct. 23, 1987

[51] Int. Cl.$^4$ ................................................ A61K 9/24
[52] U.S. Cl. .................................... 424/443; 424/446; 424/447; 424/448; 424/449
[58] Field of Search ................ 424/443, 446, 447, 448, 424/449

[56] References Cited

U.S. PATENT DOCUMENTS

| | | | |
|---|---|---|---|
| Re. 27,401 | 6/1972 | Wichterle et al. | 524/916 |
| 3,520,949 | 7/1970 | Shepherd et al. | 525/193 |
| 4,177,056 | 12/1979 | Mueller et al. | 424/78 |
| 4,568,343 | 2/1986 | Leeper et al. | 424/449 |
| 4,588,580 | 5/1986 | Gale et al. | 424/21 |
| 4,668,506 | 5/1987 | Bawa | 424/429 |

OTHER PUBLICATIONS

Evans et al: J. Pediatr., vol. 107, pp. 307–311 (1985), "Percutaneous Theophylline Administration to Preterm Infant".
Kurihara–Bergstrom et al.: J. of Controlled Release, vol. 6, pp. 51–58 (1987), "Skin Development and Permeability".
Evans et al: Intl. Journal of Pharaceutics, vol. 24, pp. 259–265 (1985), "Transdermal Drug Delivery to Neonates".
Hadgraft et al: Proceedings Intern. Symp. Contr. Rel. Broact. Mater., vol. 12, pp. 349–350 (1985), "Transdermal Drug Delivery to the Neonate".
Evans et al: J. Pharm. Pharmacol, vol. 36, No. 12, p. 10p (1984), Theophylline 767, "In Vitro Release of Theophylline with a View to Systemic Percutaneous Treatment in the Preterm Infant".
Barker et al: J. Invest. Dermat., vol. 88, pp. 409–411 (1987), "Skin Permeability in the Newborn".

Primary Examiner—Ellis P. Robinson
Assistant Examiner—P. J. Ryan
Attorney, Agent, or Firm—Irving M. Fishman

[57] ABSTRACT

A method of treating a premature neonatal infant of a gestational age between about 24 and about 35 weeks with a pharmaceutically acceptable, systemically active, substantially skin compatible, water-soluble neonatal therapeutic agent having a molecular weight below about 5000, and which agent is substantially non-transmissable through normal mature intact human skin, comprising:

(a) applying to the intact neonatal skin of said infant a transdermal device comprising (i) a backing member, (ii) a substantially shape retaining hydrogel reservoir having a water content of between about 5 percent and about 95 percent preferably between 10 percent and 80 percent by weight of said reservoir and containing an effective amount of said agent, (iii) a skin contacting surface of predetermined area, and (iv) means for maintaining said reservoir in material transmitting relationship to said skin;

(b) maintaining said skin contacting surface of said device in material transmitting relationship to said intact neonatal skin of the infant for an extended period of time; and (c) delivering said agent through the intact neonatal skin in a controlled continuous manner such that the blood plasma level of said agent is substantially within the therapeutic index of said agent for a majority of said extended period of time.

9 Claims, No Drawings

TRANSDERMAL ADMINISTRATION OF A SYSTEMIC ACTIVE AGENT TO A PREMATURE NEONATAL INFANT

BACKGROUND OF THE INVENTION

The present invention relates to a method of treating a premature neonatal infant with a systemic therapeutic agent transdermally through the intact skin of the infant.

The normal methods of administering systemically active therapeutic agents to preterm infants have distinct drawbacks. Oral administration of such agents generally leads to unpredictable absorption from the undeveloped gastrointestinal tract. Intravenous administration generally requires an access line which has a large dead volume compared with the generally small volume required by the patient. Moreover, the rather fragile and tiny vein size further introduces complications in attempts to administer drugs intravenously in such infants. Further, in preterm infants, inherent dangers are introduced due to the generally narrow therapeutic index of many neonatal therapeutic agents.

The main factor governing percutaneous absorption of an active agent is the permeability barrier function of the skin. However, in premature neonates, the stratum corneum is poorly developed. As a result, the skin of the preterm infant is extremely permeable. Thus, for example, systemically toxic agents applied to the skin of neonates has been reported to result in accidental illness and death. See for example, H. Powell et al., "Hexachlorophene Myelinopathy in Premature Infants", *J. Pediatrics*, Vol. 82, pp. 976–981 (1973); B. M. Kagan et al, "Cyanosis in Premature Infants Due to Aniline Dye Intoxication", *J. Pediatrics*, Vol. 34, p. 574–578 (1949).

Attempts have been made to deliver a systemic active agent, theophylline in the form of the sodium glycinate salt, to premature neonatal infants by the use of an hydroxymethylcellulose gel placed on the neonate abdominal skin over a 2 cm² diameter area under an occlusive patch. However, in all cases removal of the patch was reported as necessary due to leakage of the gel after 48 hours. See J. Hadgraft et al, "Transdermal Drug Delivery to the Neonate", *Proceed. Intern. Symp. Control. Rel. Bioact. Mater.*, Vol. 12, pp. 349–350 (1985).

It is therefore an object of the present invention to provide a method of administering a systemically active agent which overcomes many of the drawbacks associated with the aformentioned techniques. More specifically, it is an object of the present invention to use the extremely permeable nature of the preterm neonate to transdermally deliver pharmaceutically acceptable systemically active agents to the neonate through intact skin while avoiding the drawbacks associated with a flowable gel.

It is a further object of the invention to provide a transdermal device for use in such a method.

These and other objects of the present invention are apparent from the following specific disclosures.

DETAILED DESCRIPTION OF THE INVENTION

One embodiment of the instant invention relates to a method of treating a premature neonatal infant of a gestational age between about 24 and about 36 weeks with a pharmaceutically acceptable, systemically active, substantially skin compatible, water-soluble neonatal therapeutic agent, which is substantially non-transmissable through normal mature intact human skin, and said agent having a molecular weight below about 5000, comprising:

(a) applying to the intact skin of said infant a transdermal device comprising (i) a backing member, (ii) a substantially shape retaining hydrogel reservoir having a water content between about 5 percent and about 95 percent by weight of said reservoir and containing an effective amount of said agent, (iii) a skin contacting surface of predetermined area, and (iv) means for maintaining said reservoir in material transmitting relationship to said skin;

(b) maintaining said skin contacting surface of said device in material transmitting relationship to said intact skin of the infant for an extended period of time; and (c) deliverying said agent through the intact skin in a controlled continuous manner such that the blood plasma level of said agent is substantially within the therapeutic index of said agent for a majority of said extended period of time.

Suitable pharmaceutically acceptable systemically active, substantially skin compatible water-soluble neonatal therapeutic agents constitute a general known class of products.

Suitable therapeutic agents include antibiotics, cardiovascular, respiratory and metabolic agents, vitamins, anticoagulants, anticonvulsants, antidotes, diuretics and the like.

Specific therapeutic agents which have been used in infant therapy include for example adrenergics, such as dobutamine, dopamine, epinephrine and isoproterenol; antibacterials such as amikacin, ampicillin, carbencillin, cefazolin, ceftriaxone, chloramphenicol, clindamycin, erythromycin estolate, gentamycin, kanamycin, methicillin, moxalactam, nafcillin, oxacillin, penicillin G, piperacillin, ticarcillin, tobramycin, trimethoprim, sulfamethoxazole and vancomycin ; antifungals, such as amphotericin B, 5-fluorocytosine, miconazole and nystatin; antituberculous agents, such as isoniazid, rifampin and streptomycin; antiviral agents such as adenine arabinoside; anticoagulants, such as heparin; thyroid agents, such as methimazole, propylthiouracil and triiodothyronine; sedatives, tranquilizers or pain relivers, such as chloral hydrate, diazepam, chlorpromazine, promethazine, morphine and meperidine; vitamins, such as thiamine, riboflavin, pyridoxine, alphatocopherol hemisuccinate, cyanocobalamine, and ascorbic acid; anticonvulsants, such as carbamazepine, paraldehyde, phenobarbital, and valproic acid; antidotes, such as atropine, methylene blue, naloxone and protamine; cardiovascular agents such as diazoxide, digoxin, hydralazine, lidocaine, nitroprusside, procainamide, propanolol, atenolol, metoprolal, tolazoline, verapamil, neostigmine and pyridostigmine; cholinergic blocking agents, such as belladonna; cholinesterase inhibitors such as edrophonium; diuretics, such as acetazolamide, chlorothiazide, hydrochlorothiazide, ethacrynic acid, furosemide, and spironolactone; adrenal agents, such as ACTH, hydrocortisone, and prednisone; pancreatic agents, such as glucagon, and insulin; pituitary agents, such as vasopressin; and miscellaneous agents, such as indomethacin, diclofenac, terbutaline, theophylline, aminophylline, caffeine, chloroquine, kayexalate, methadone, pancuronium bromide and cimetidine. Advantageously, the therapeutic agent is in its water-soluble pharmaceutically acceptable form, such as its conventional pharmaceutically acceptable salt, hydrate, complex or pro-drug ester.

Preferred neonatal therapeutic agents include theophylline, eg. in the form of its choline salt, gentamicin, terbutaline, eg. in the form of its sulfate salt, diclofenac, phenobarbital, eg. in the form of its sodium or ethanolamine salt, and digoxin. Most preferred is theophylline, eg. in the form of a water soluble pharmaceutically acceptable salt thereof, especially the choline salt thereof.

The therapeutic agent is one which is substantially non-transmissable through normal mature intact skin, such as the intact skin of an infant at full term where the stratum corneum is fully developed. By substantially non-transmissable in this context is meant that the agent, eg. in the form of an aqueous solution thereof, or the like, does not migrate through fully developed skin at a rate such that the blood plasma level of said agent reaches therapeutically effective levels of such agent. Generally, the rate of migration of such agents through mature intact skin is less than one-half the rate of migration of such agents through intact neonatal skin, per unit area of skin contacting surface.

By "water-soluble" in relationship to the therapeutic agent is meant an agent which is sufficiently soluble in the aqueous hydrogel medium such that an effective therapeutic amount is released from the reservoir through the skin over a given area and such that a therapeutically effective level, within the therapeutic index, is maintained over an extracted period of time. For example, if the agent is highly soluble in water, the reservoir may contain all of the agent in solution. Alternatively, the agent may be dispensed within the matrix, e.g. in the form of depots, which, upon application, dissolve into the reservoir at the same rate that the agent is delivered by the reservoir to the neonate skin. Moreover, the agent may be placed in a suitable manner, e.g. as a homogeneous aqueous solution or suspension, between the backing membrane and the hydrogel reservoir, in the form of a microporous sponge matrix or active agent permeable container. Here again, as the active agent is released through the skin from the hydrogel reservoir, the hydrogel reservoir will absorb active agent from the sponge matrix or active agent permeable container.

Suitable hydrogel materials for use as a reservoir include those crosslinked hydrophilic polymers which have been disclosed as compatible with human tissue, such as hydrogels described as useful in body implants or soft hydrophilic contact lens materials. In general such materials contain, upon equilibration with water, between about 5 and about 95 percent preferably between 10 percent and 80 percent water by weight. Useful polymers include those crosslinked hydrogel polymers described, for example in U.S. Pat. No. 3,220,960, U.S. Pat. No. Re. 27,401, U.S. Pat. Nos. 3,520,949, 2,410,949, 4,177,056, and U.S. Pat. No. 4,177,056. For example, suitable crosslinked hydrogels include those prepared by copolymerization of a major amount of a hydrophilic mono-olefinic monomer and a minor amount of a hydrophilic or hydrophobic crosslinking agent. In order to increase the lipophilicity of the hydrogel, there may also be present, in addition to the hydrophilic mono-olefin, a minor amount of a hydrophobic mono-olefin. Alternatively, there may be employed a hydrogel prepared by copolymerizing di- or polyvinylic macromer with a mono-olefinic monomer, or mixture of monomers, having sufficient hydrophilicity such that the resulting polymer is capable, upon equilibration, of absorbing between about 5 and about 95 percent preferably between 10 percent and 80 percent by weight water, based upon the total weight of the equilibrated polymer hydrogel.

The drug loaded swollen hydrogel is maintained in a transmitting relationship with the neonate skin by means known per se in the art. For example, the hydrogel may be maintained on the skin by means of an adhesive ring or the like attached, for example, to the backing member; or by use of a flexible strap attached to the device, e.g., to the backing member thereof; or by means of a drug transmissible adhesive interposed between the hydrogel reservoir and the neonate skin. Other equivalent means are well known in the art.

Preferably, the backing member is constructed of a material which is substantially impermeable to the aqueous drug containing medium, in order to retard evaporation of the reservoir, e.g., in storage or during extended application.

The patch size, in terms of skin contacting area may vary widely, depending on the drug employed and the therapeutic benefit desired. Preferably, the skin contacting surface area of the device is between about 0.5 and about 20 cm$^2$, more preferably between about 0.5 and about 10 cm$^2$.

In order to efficiently transmit the active agent through the neonate skin, the drug chosen should desirably possess a drug flux between about 0.1 and about 1000 $\mu$g/cm$^2$/hr, more preferably between about 0.2 to about 500 $\mu$g/cm$^2$/hr, most preferably between about 0.5 to about 300 $\mu$g/cm$^2$/hr.

Generally, the device is designed to remain in active drug transmitting relationship for delivery of the agent within the drug therapeutic index, e.g., as measured in terms of drug plasma level, for a period of at least about 6 hours, preferably between about 12 hours and about 10 days, most preferably between about 1 day and about 8 days.

The following examples are for illustrative purposes only and are not intended to limit the scope of the invention. All parts are by weight unless otherwise disclosed.

EXAMPLE 1

The hydrogel disks used in the following examples were prepared as follows:

A. Two thousand parts (1 mole) of poly-tetramethylene oxide having a molecular weight of about 2000 (Polymeg 2000) are melted and poured into a 5 liter 3-neck flask and heated to 80° C. for one hour under vacuum to remove moisture. The vacuum is broken with dry nitrogen and the contents cooled to 40° C. To the flask there is added 444.6 parts (2 moles) of isophorone diisocyanate followed by 1 g triethylamine and the temperature is raised to 80° C. After 5 hours the NCO content has dropped to about 3.50 percent, as determined by titration, and the mixture is cooled to 40° C., to obtain the isocyanate capped product.

B. To 25 parts of the aforementioned isocyanate capped product there is added, incrementally, approximately 250 parts of 2-hydroxyethyl methacrylate (HEMA) and about 0.0025 parts dibutyltin dilaurate. The mixture is left to cool to room temperature under a nitrogen blanket. Upon termination of the reaction all NCO had disappeared as measured by IR. To the resulting mixture of bis methacrylate macromer and excess HEMA there is added 0.20% by weight t-butylperoctoate at a temperature of 100° C. for one hour in glass molds lined with Mylar polyester sheets. The molds have an area of approximately 30×30 cm and a height of about 0.8 mm. Upon polymerization, the hydrogel sheet product is cooled to room temperature, swollen with distilled water for 24 hours, and disks having an area of 2 square centimeters per side are punched out of the swollen hydrogel sheet, and the disks are vacuum dried.

Purification of the dried polymer disks is achieved by a 36 hour soxhlet extraction using absolute ethanol, followed by a further 4 hour extraction using methylene chloride, and dried. In the same manner, disks having a per side area of 4 cm² and 5 cm² were similarly prepared.

EXAMPLE 2

Choline theophylline is loaded into the hydrogel disks of Example 1 as follows:

Ten disks are loaded from a substantially saturated choline theophylline solution in distilled water having a concentration of about 860 mg/ml solution and a density of about 1.17 g/ml, by placing the dried disks (having a surface area per side of 4 cm²) into said solution and loaded over a period of 10 days at a temperature of 37° C. In order to determine the extent of loading, representative samples were analyzed with the following results:

| Sample | Weight of Swollen Loaded Hydrogel (mg) | Weight of Drug (mg) |
|---|---|---|
| 1 | 603.6 | 239.8 |
| 2 | 607.0 | 242.3 |
| 3 | 613.1 | 246.8 |

In order to determine release characteristics of the drug loaded swollen disks the diffusivity of the drug from the disks were measured.

| Sample | Swollen Disk Thickness (cm) | Diffusivity (cm²/hr) |
|---|---|---|
| 1 | 0.0826 | $19.16 \times 10^{-4}$ |
| 2 | 0.0831 | $19.62 \times 10^{-4}$ |
| 3 | 0.0815 | $19.13 \times 10^{-4}$ |

In the above diffusivity determination the release was measured at 37° C. into 0.067 M phosphate buffer solution having a pH of 7.4.

EXAMPLE 3

A series of disks according to Example 1 having a per side surface area of 2 cm² were loaded from an aqueous choline theophylline solution having a concentration of choline theophylline of 454 mg/ml. Each disk contained in the swollen, loaded state approximately 35 mg theophylline (measured as theophylline base).

EXAMPLE 4

Baby A, female, 26 weeks gestational age and a postnatal age of 2 days and having a birthweight of 1.06 kilograms exhibiting apneic syndrome. The infant was treated by application of a disk prepared according to Example 3 with the following results:

| Time (hr) | Plasma Concentration Theophylline (μg/ml) |
|---|---|
| 0 | 0 |
| 3 | 8 |
| 10 | 11 |
| 25 | 11.7 |
| 40 | 11.4 |
| 80 | 6 |
| 110 | 5 |
| 125 | 4.8 |

As shown by the above, the therapeutic index (between 4 and 12 μg/ml theophylline in blood plasma) is reached within 3 hours and is maintained for a period of at least 125 hours.

What is claimed is:

1. A method of treating a premature neonatal infant of a gestational age between about 24 and about 36 weeks with a pharmaceutically acceptable, systemically active, substantially skin compatible, water-soluble neonatal therapeutic agent having molecular weight below about 5000, and which agent is substantially non-transmissable through normal mature full term infant intact human skin, comprising:
   (a) applying to the intact neonatal skin of said infant of gestational age between about 24 and about 36 weeks a transdermal device comprising (i) a backing member, (ii) a substantially shape retaining hydrogel reservoir having a water content of between about 5 percent and about 95 percent preferably between 10 percent and 80 percent by weight of said reservoir and containing an effective amount of said agent which is substantially non-transmissable through normal mature intact human skin, (iii) a skin contacting surface of predetermined area, and (iv) means for maintaining said reservoir in material transmitting relationship to said skin;
   (b) maintaining said skin contacting surface of said device in material transmitting relationship to said intact neonatal skin of the infant for an extend period of time; and
   (c) delivering said agent through the intact neonatal skin in a controlled continuous manner such that the blood plasma level of said agent is substantially within the therapeutic index of said agent is substantially within the therapeutic index of said agent for a majority of said extended period of time.

2. A method according to claim 1, wherein the hydrogel is a crosslinked hydrophilic polymer.

3. A method according to claim 1, wherein the hydrogel contains between about 10 percent and about 80 percent water by weight, based upon the weight of hydrogel.

4. A method according to claim 1, wherein said backing member is substantially impermeable to the reservoir.

5. A method according to claim 1, wherein the skin contacting surface area of the device is between about 0.5 and about 20 cm².

6. A method according to claim 1, wherein said extended period of time is between about 12 hours and about 10 days.

7. A method according to claim 1, wherein said water soluble neonatal therapeutic agent is selected from the group consisting of an antibiotic, a cardiovascular, respiratory or metabolic agent, a vitamin, an anticoagulant, an anticonvulsant, an antidote or a diuretic.

8. A method according to claim 7, wherein said agent is a water-soluble pharmaceutically acceptable salt of theophylline.

9. A method according to claim 8, wherein said agent is choline theophylline.

* * * * *